US012605088B2

(12) United States Patent
Rossi et al.

(10) Patent No.: US 12,605,088 B2
(45) Date of Patent: Apr. 21, 2026

(54) METHOD FOR DETERMINING RESPIRATORY TIMING PARAMETERS FROM RESPIRATORY MONITORING MEASUREMENTS OF A SUBJECT

(71) Applicant: Onera Technologies B.V., Eindhoven (NL)

(72) Inventors: Alessandro Rossi, Eindhoven (NL); Hartmut Schneider, Eindhoven (NL)

(73) Assignee: Onera Technologies B.V., Eindhoven (NL)

( * ) Notice: Subject to any disclaimer, the term of this patent is extended or adjusted under 35 U.S.C. 154(b) by 352 days.

(21) Appl. No.: 18/281,508

(22) PCT Filed: Mar. 8, 2022

(86) PCT No.: PCT/EP2022/055887
§ 371 (c)(1),
(2) Date: Sep. 11, 2023

(87) PCT Pub. No.: WO2022/189429
PCT Pub. Date: Sep. 15, 2022

(65) Prior Publication Data
US 2024/0164660 A1    May 23, 2024

(30) Foreign Application Priority Data
Mar. 12, 2021    (EP) ..................................... 21162260

(51) Int. Cl.
*A61B 5/087*        (2006.01)
*A61B 5/08*         (2006.01)
*A61B 5/085*        (2006.01)
(52) U.S. Cl.
CPC ............ *A61B 5/0871* (2013.01); *A61B 5/086* (2025.01)

(58) Field of Classification Search
CPC ..... A61B 5/0816; A61B 5/0871; A61B 5/086; A61B 5/087; A61B 5/7235; A61B 5/7239; A61B 5/725
See application file for complete search history.

(56) References Cited

U.S. PATENT DOCUMENTS

2009/0118626 A1* 5/2009 Moon ................... A61B 5/086
                                                    600/484
2014/0228905 A1    8/2014 Bolea

FOREIGN PATENT DOCUMENTS

WO        2020255128 A1    12/2020

OTHER PUBLICATIONS

International Search Report for International Application No. PCT/EP2022/055887, mailed Jun. 24, 2022, (3 pages).
(Continued)

*Primary Examiner* — Chu Chuan Liu
(74) *Attorney, Agent, or Firm* — Kagan Binder, PLLC

(57) ABSTRACT

The present disclosure relates to a method (MO) for providing respiratory timing parameters from respiratory monitoring measurements of a subject, the method comprising the steps of: providing (M1) a respiratory effort signal (E) and a respiratory flow signal (F) of a subject; determining (M2a) an ensemble of peaks (pE) in the respiratory effort signal (E) and determining (M2b) an ensemble of valleys (vE) in the respiratory effort signal (E); and identifying (M3) times associated with the valleys (vE) as preliminary inspiratory onset times (t'io); refining (M4) preliminary inspiratory onset times (t'io) within respective peak-to-peak time intervals (Tpp) of the respiratory effort signal (E) by: determining (M41) first derivative (F1d) of the respiratory flow signal (F) in a respective peak-to-peak interval (Tpp); determining (M42) local peaks (pF1d) and valleys (vF1d) in the respiratory flow signal first derivative (F1d); determining (M43) a time midpoint (tmid) between the time of a local
(Continued)

valley (vF1$d$) in the respiratory flow signal first derivative (F1$d$) closest in time to the later endpoint in the respective peak-to-peak time interval (Tpp) and the time of a local peak (pF1$d$) in the respiratory flow signal derivative (F1$d$) in the respective peak-to-peak time interval (Tpp); evaluating (M44) whether the respiratory effort signal (E) at the determined time midpoint (tmid) satisfies a predetermined inspiratory onset time condition, and if satisfied, selecting (M45) the determined time midpoint (tmid) as an inspiratory onset time (tio) instead of the preliminary inspiratory onset time (t'io) for that peak-to-peak interval (Tpp), whereas if the condition is not satisfied, keep the preliminary inspiratory onset time as the inspiratory onset time for that peak-to-peak interval.

20 Claims, 6 Drawing Sheets

(56) References Cited

OTHER PUBLICATIONS

Hult et al., "A bioacoustic method for timing of the different phases of the breathing cycle and monitoring of breathing frequency," Medical Engineering & Physics, vol. 22, No. 6, pp. 425-433, Jul. 1, 2000, (9 pages).

\* cited by examiner

Respiratory rate [bpm] over time

+Ti (solid black) and -Te (white) [sec] over time

Duty cycle [%]

METHOD FOR DETERMINING RESPIRATORY TIMING PARAMETERS FROM RESPIRATORY MONITORING MEASUREMENTS OF A SUBJECT

CROSS-REFERENCE TO RELATED APPLICATIONS

This application claims priority to International Application No. PCT/EP2022/055887, filed Mar. 8, 2022 and titled "METHOD FOR DETERMINING RESPIRATORY TIMING PARAMETERS FROM RESPIRATORY MONITORING MEASUREMENTS OF A SUBJECT," which in turn claims priority from a European Patent Application having Ser. No. 21/162,260.0, filed Mar. 12, 2021, all of which are incorporated herein by reference in their entireties.

TECHNICAL FIELD

The present inventive concept relates to a method for determining respiratory timing parameters from respiratory monitoring measurements of a subject and a device for doing the same. In particular, the present inventive concept relates to detecting expiratory onset times and inspiratory onset times, as well as refining inspiratory onset times, from respiratory monitoring measurements including but not limited to respiratory effort signal and respiratory flow signal measurements.

BACKGROUND

In many medical instances, it is of interest to monitor and determine parameters which facilitate quantifying various aspects of respiration. Respiratory drive or performance may be determined via conventional means such as esophageal lung pressure measurements or via assessment of respiratory duty cycles and respiratory rate. Esophageal lung pressure measurements are invasive and thus more cumbersome to perform. Respiratory duty cycles and/or respiratory rate (RR) require as an input a respiratory signal which is in phase with the respiration of the subject.

One promising option is to assess respiratory duty cycles, DC (RDC), also called inspiratory duty cycles (IDC), and respiratory rates, RR, based on oscillatory signals obtained via respiratory monitoring measurements of a subject. Such respiratory monitoring measurements may include measurement belts, accelerometers, cannulas, etc. It may also include bio-impedance measurements of the subject. It is important to track respiratory rate and duty cycle separately so that respiratory components that affect the so called "effective ventilation" may be independently monitored. Moreover, monitoring duty cycle is also very relevant for detecting a condition called "flow limitation", which typically elicits an increase in duty cycle in order to preserve the so called "minute ventilation".

Such solutions based on oscillatory signals put great emphasize on quality of measurements and digital filtering of signals which preserve the desired information while reducing noise. However, the technical field of digital filtering is expansive due to many decades of research and it is therefore difficult to find solutions which prove effective for the application of determining respiratory timing parameters from respiratory monitoring measurements.

Thus, there is a need for an improved method which prove effective for determining respiratory timing parameters from respiratory monitoring measurements of a subject. It would further be desirable for such a method which relies on non-invasive respiration monitoring measurements of a subject.

SUMMARY

It is an object of the present invention concept to provide an improved solution that alleviates the mentioned drawbacks with present solutions. Furthermore, it is an object to provide a method which prove effective for determining respiratory timing parameters from respiratory monitoring measurements of a subject. A further object is to provide a method which relies on non-invasive respiration monitoring measurements of a subject.

These objects of the present inventive concept are at least partly met by the invention as defined in the independent claims. Preferred embodiments are set out in the dependent claims. Further embodiments are also disclosed in this summary and in the detailed description.

According to a first aspect of the invention, this is provided by a method for providing respiratory timing parameters from respiratory monitoring measurements of a subject, the method comprising the steps of: providing a respiratory effort signal and a respiratory flow signal of a subject; determining an ensemble of peaks in the respiratory effort signal and determining an ensemble of valleys in the respiratory effort signal; identifying times associated with the peaks as expiratory onset times, and identifying times associated with the valleys as preliminary inspiratory onset times; refining preliminary inspiratory onset times within respective peak-to-peak time intervals of the respiratory effort signal by: determining first derivative of the respiratory flow signal in a respective peak-to-peak interval; determining local peaks and valleys in the respiratory flow signal first derivative; determining time midpoint between the time of a local valley in the respiratory flow signal first derivative closest in time to the later endpoint in the respective peak-to-peak time interval and the time of a local peak in the respiratory flow signal derivative in the respective peak-to-peak time interval; evaluating whether the respiratory effort signal at the determined time midpoint satisfies a predetermined inspiratory onset time condition, and if satisfied, selecting the determined time midpoint as an inspiratory onset time instead of the preliminary inspiratory onset time for that peak-to-peak interval, whereas if the condition is not satisfied, keep the preliminary inspiratory onset time as the inspiratory onset time for that peak-to-peak interval.

By this method, refined inspiratory onset times are provided. In particular, the method provides a series of inspiratory onset times which are adjusted in time relative inspiratory onset times determined according to conventional methods. The time-adjusted inspiratory onset times may result in more consistent datapoints, thereby improving precision. This may further enable assessment of respiration when based on respiratory effort and respiratory flow signals with considerable and higher noise levels.

Further, an advantage of this method is respiratory rate and duty cycle can be tracked separately so that respiratory components that affect the so called "effective ventilation" may be independently monitored.

By "respiratory effort", we hereby intend any signal that tracks changes in physiological quantities rhythmically related to breathing mechanics and/or volume changes, as for instance smoothed bioimpedance signals, thoracic and/or abdominal movements acquired with belt signals, esophageal pressure signals, plethysmography signals, accelerometer signals acquired on the chest and/or abdomen, and more.

By "respiratory flow", we hereby intend any signal that represents airflow through lungs and/or bronchi and/or upper airways, such as for instance flow signals obtained by processing bioimpedance signals, nasal pressure cannula signals, pneumotachograph signals, and more.

As for the respiratory monitoring measurements of a subject, these at least include measurements by which a respiratory effort signal and a respiratory flow signal of a subject can be extracted. Such measurements may for example include bio-impedance measurements, nasal pressure cannulas, thorax belts, accelerometers, pneumotachographs etc.

The information constituting the respiratory effort signal and the respiratory flow signal may be provided as either continuous-time signals or as discrete-time signals or a mix between the two. For example, the respiratory effort signal may be provided as a continuous-time signal and the respiratory flow signal may be provided as a discrete-time signal. Alternatively, the respiratory effort signal may be provided as a discrete-time signal and the respiratory flow signal may be provided as a continuous-time signal. In case of discrete-time signals, a sampling rate of 16-256 samples per second may be used. Alternatively, 32-128 samples per second may be used, or 50-80 samples per second may be used. The sampling rate may be a selected sampling rate value selected from sampling rate intervals of 10-20 samples per second, 20-30 samples per second, 30-40 samples per second, 40-50 samples per second, 50-60 samples per second, 60-70 samples per second, 70-80 samples per second, 80-90 samples per second, 90-100 samples per second, or 100-110 samples per second, 110-120 samples per second, 120-130 samples per second, 130-140 samples per second, or more samples per second. The sampling rate may vary in a cyclical behavior so that more or less samples are used during time segments of the respective signal for particular segments.

Further, the respiratory monitoring measurements may be ongoing as the method is performed. Alternatively, the respiratory monitoring measurements may have been completed and the method is performed at a later time.

The method steps of the method may be provided in the form of computer readable instructions executable by a processing device. The method steps may thus be performed by means of a processing device.

The peak and valley detection steps in the method may incorporate peak detection according to standard peak detection methods. Here, "associated to" or "associated with" may mean the times at which each determined peak occurs.

Further, the method involves determining peak-to-peak intervals of the respiratory effort signal. This is done by cycling between pairs of consecutive peaks and identifying the time interval between when the associated times at which these occur. These associated times then constitutes the endpoints for each respective peak-to-peak interval. Thereafter, the valleys and peaks in the respiratory flow signal derivative is inspected within each peak-to-peak interval when determining the respective inspiratory onset time. The valley closest in time to the latest endpoint in the respective peak-to-peak interval may be taken into consideration when determining the inspiratory onset time for this peak-to-peak interval. The inspiratory onset time may be determined as the midpoint between this valley and a peak within the respiratory flow signal derivative.

The predetermined inspiratory onset time condition may be a condition that is sufficient to ensure that the resulting inspiratory onset times provide a qualitatively improved foundation for respiratory effort assessment to be carried out. By refining the inspiratory onset times, it may increase the probability that the inspiratory onset times are selected more favorably so that the resulting inspiratory onset times are improved quality-wise.

According to one embodiment, the respiratory effort signal and the respiratory flow signal are obtained via non-invasive respiratory monitoring measurements. Such non-invasive respiratory monitoring measurements may include bio-impedance signal measurements, nasal pressure cannulas, thorax belts, accelerometers, pneumotachographs and more.

According to one embodiment, the respiratory effort signal and the respiratory flow signal are obtained via bio-impedance signal measurements. Bio-impedance signal measurements may be made by means of electrodes arranged on the subject. The electrodes may be arranged on the torso of the subject. The electrodes may be arranged in a bipolar or tetrapolar configuration. More than four electrodes may be used during bio-impedance signal measurements. The electrodes may be incorporated into a wearable patch device. The respiratory effort signal and the respiratory flow signal may be extracted from such a bio-impedance signal. These may be extracted by first having extracted the respiratory effort signal from the bio-impedance signal using filtering and processing methods. The respiratory flow signal may then be obtained by derivation of the respiratory effort signal.

According to one embodiment, the predetermined inspiratory onset time condition is whether the amplitude range of the respiratory effort signal at the inspiratory onset time to the subsequent expiratory onset time is at least 75% of the amplitude range of the respiratory effort signal as measured from the preliminary inspiratory onset time to the following expiratory onset time. By this, it may increase the likelihood that determined valleys are the most significant valleys for each cycle and not a local valley. The predetermined inspiratory onset time condition may be at least 80%, 85%, or 90% etc.

According to one embodiment, the step of determining first derivative of the respiratory flow signal includes using a Savitsky-Golay derivative kernel incorporating a $2^{nd}$ degree polynomial fit. This may provide well behaved respiratory flow signal derivative. In particular, the respiratory flow signal derivative may be ensured to be smooth by this in the case that the respiratory flow signal is determined by derivation of the respiratory effort signal using a Savitsky-Golay derivative kernel.

According to one embodiment, the Savitsky-Golay derivative kernel is characterized by a frame length equal to or less than 150 ms, preferably less than 120 ms. By this, the respiratory flow signal derivative may be smoother and thus well-behaved in further processing steps, such as during peak and valley detection.

According to one embodiment, the step of determining an ensemble of peaks in the respiratory effort signal includes selecting peaks determined to have a prominence greater than an average prominence determined over a sub segment of the respiratory effort signal. The average prominence may be taken as the standard deviation over said sub-segment divided by the square root of two. The average prominence may be taken as the standard deviation over said sub-segment multiplicated by a scaling factor. The scaling factor may be selected from an interval of zero-point-five and one, e.g. zero-point-seven. The average prominence will be updated over time as the sub-segment changes; thus, this average prominence may be considered an adaptive peak prominence.

According to one embodiment, the step of determining an ensemble of valleys in the respiratory effort signal includes inverting a sub segment of the respiratory effort signal and selecting peaks determined to have a prominence greater than an average prominence determined over said inverted sub segment. The average prominence may be taken as the standard deviation over said sub-segment divided by the square root of two. The average prominence may be taken as the standard deviation over said sub-segment multiplicated by a scaling factor. The scaling factor may be selected from an interval of zero-point-five and one. It may be approximately or exactly zero-point-seven. The average prominence will be updated over time as the sub-segment changes; thus, this average prominence may be considered an adaptive peak prominence.

According to one embodiment, the length of either sub segment, or both, is between 10 and 15 seconds. Here, sub-segments refer to the sub-segment over which the adaptive peak prominence is determined. The length of either sub-segment, or both, is in a more preferred embodiment between 11 and 13 seconds, and in a most preferred embodiment about 12 seconds. Other lengths of either sub segment, or both, may be used.

According to one embodiment, the method comprises the step of: determining if there is missing any determined valleys between any two consecutive peaks in the ensemble of peaks, and if so, inverting the two-consecutive-peak segment missing a determined valley and determining the location of the undetermined valley by peak detection using half of the two-consecutive-peak segment's dynamic range as a minimum prominence threshold, and if unable to determine a valley still, determining the location of the undetermined valley as the midpoint between the two consecutive peaks. By this, it may be ensured that all of the significant valleys are accounted for in the respiratory effort signal which then may result in denser data points for inspiratory onset times.

According to one embodiment, the method comprises the step of: determining if there is missing any determined peaks between any two consecutive valleys in the ensemble of valleys, and if so, determining the location of the undetermined peak in the two-consecutive-valley segment missing a determined peak by peak detection using half of the two-consecutive-valley segment's dynamic range as a minimum prominence threshold, and if unable to determine a peak still, determining the location of the undetermined peak as the midpoint between the two consecutive valleys. By this, it may be ensured that all of the significant peaks are accounted for in the respiratory effort signal which then may result in denser data points for inspiratory onset times.

According to one embodiment, the step of determining peaks and valleys in the respiratory flow signal derivative includes using more than a predetermined ratio of a local dynamic range as minimum peak prominence. By this, noise may be filtered. The predetermined ratio may be equal to or more than 5-10%. By this, more noise may be filtered while preserving key information within the signal.

According to one embodiment, the step of determining inspiratory onset times includes using peaks in the respiratory flow signal first derivative which are the closest, but no closer than a predetermined time offset, to the latest endpoint of the respective peak-to-peak time interval. By this, the inspiratory onset times may be determined in a more consistent manner. The predetermined time offset is preferably less than 200 milliseconds, more preferably less than 160 milliseconds. By this, a specific peak may be aimed for when determining the inspiratory onset times, thereby ensuring the inspiratory onset times to be determined in a consistent manner.

According to one embodiment, the method comprises the step of identifying times associated with the peaks of the ensemble of peaks of the respiratory effort signal as expiratory onset times and preferably determining whether the inspiratory onset times and the expiratory onset times are equal in number. By identifying times associated with the peaks of the ensemble of peaks of the respiratory effort signal as expiratory onset times, a set of expiratory and inspiratory onset times is provided. Using these respiratory timing parameters, further respiratory timing parameters may be determined. Moreover, by preferably determining whether the inspiratory onset times and the expiratory onset times are equal in number, it may be ensured that no inspiratory onset times or expiratory onset times have been missed. If it is determined to be the case, the method may comprise a step of determining which inspiratory onset time(s) and/or expiratory onset time(s) are missing and remove previous or subsequent expiratory onset time(s) and/or inspiratory onset time(s) so that for every sub-segment analyzed, there is an equal number of onset times. In principle, this allows for the removal of unreliable breaths from data analysis.

According to one embodiment, the method comprises the step of determining a first respiration parameter being an inspiratory time interval by taking expiratory onset time and subtracting from it the previous inspiratory onset time. This first respiration parameter may be determined in a continuous manner during ongoing measurements. The first respiration parameter may be displayed on a display, thereby enabling monitoring of said first respiration parameter.

According to one embodiment, the method comprises the step of determining a second respiration parameter being an expiratory time interval by taking inspiratory onset time and subtracting from it the previous expiratory onset time. This second respiration parameter may be determined in a continuous manner during ongoing measurements. The second respiration parameter may be displayed on a display, thereby enabling monitoring of said second respiration parameter.

According to one embodiment, the method comprises the step of determining a breath-by-breath respiratory rate by taking the reciprocal of the sum of the inspiratory time interval and the expiratory time interval. This respiratory rate may be determined in a continuous manner during ongoing measurements. The respiratory rate may be displayed on a display, thereby enabling monitoring of the respiratory rate.

According to one embodiment, the method comprises the step of determining a breath-by-breath inspiratory duty cycle by multiplying the inspiratory time interval with the respiratory rate. This inspiratory duty cycle may be determined in a continuous manner during ongoing measurements. The inspiratory duty cycle may be displayed on a display, thereby enabling monitoring of the inspiratory duty cycle.

According to a second aspect of the inventive concept, a computer program is provided. The computer program may comprise instructions which, when executed by a computing device, cause the computing device to carry out the method according to first aspect or any embodiments thereof.

The computing device may be a portable computing device such as a smartphone, a smartwatch, a tablet, or a laptop. The computing device may alternatively be a workstation or a server. In case of a server, the program code may be controlled from an interface running on a remote computing device. The program code may be executed by means of cloud computing.

According to a third aspect, a program readable storage medium is provided. The program readable storage medium may store the computer program according to the second aspect.

According to a fourth aspect, a device for determining respiratory timing parameters from respiratory monitoring of a subject is provided. The device comprises a processor configured to execute the method according to the first aspect or any embodiments thereof.

The device may comprise a bio-impedance measurement sensor configured for arrangement in relation to the subject for acquiring a bio-impedance signal. The processor may be configured to receive information corresponding to the bio-impedance signal acquired by the bio-impedance measurement sensor. The processor may be configured to divide the bio-impedance signal into an effort component, i.e. a respiratory effort signal, representing a respiratory effort of the subject and a flow component, i.e. a respiratory flow signal, representing a respiratory airflow of the subject.

After having acquired the respiratory effort signal and the respiratory flow signal, the processor carries out the method for determining respiratory timing parameters. This may include expiration times and inspiration times. The processor may output these respiratory timing parameters for further analysis. The processor may further be configured to determine a first respiration parameter being an inspiratory time interval by taking expiratory onset time and subtracting from it the inspiratory onset time. The processor may be further configured to determine a second respiration parameter being an expiratory time interval by taking inspiratory onset time and subtracting from it the expiratory onset time. This second respiration parameter may be determined in a continuous manner during ongoing measurements. The second respiration parameter may be displayed on a display, thereby enabling monitoring of said second respiration parameter. The processor may be further configured to determine a respiratory rate by taking the reciprocal of the sum of the inspiratory time interval and the expiratory time interval. This respiratory rate may be determined in a continuous manner during ongoing measurements. The respiratory rate may be displayed on a display, thereby enabling monitoring of the respiratory rate. The processor may be further configured to determine an inspiratory duty cycle by multiplying the inspiratory time interval with the respiratory rate. This inspiratory duty cycle may be determined in a continuous manner during ongoing measurements. The inspiratory duty cycle may be displayed on a display, thereby enabling monitoring of the inspiratory duty cycle.

By outputting and optionally displaying any of these respiratory timing parameters, more detailed analysis of the respiration of a subject is enabled, either by automated analysis of the respiratory timing parameters, i.e. for feature extraction, or by manual analysis of the displayed respiratory timing parameters.

Bio-impedance measurement may be made by means of electrodes arranged on a thorax of a subject, for example in a tetrapolar configuration.

The bio-impedance measurement sensor may be configured for arrangement on the subject, whereby the bio-impedance measurement sensor may be configured for direct contact with the skin of the subject. However, the bio-impedance measurement sensor may alternatively be configured for arrangement in relation to the subject so as to acquire a bio-impedance signal in a non-contact relation with the subject, e.g. using capacitive coupling between the bio-impedance measurement sensor and the subject. For instance, the bio-impedance measurement sensor may be configured to be embedded in a bed, such as in a mattress, for acquiring of a bio-impedance signal of a subject lying in the bed. Similarly, the bio-impedance measurement sensor may be embedded in a chair or seat or in clothing that is worn by the subject.

Further, the device may be configured to receive the respiratory effort signal and respiratory flow signal and present determined respiratory timing parameters. Further, the respiratory timing parameters may be used to discern between two or more of obstructive sleep apnea (OSA), central sleep apnea (CSA), obstructive hypopnea, and central hypopnea.

The device may be configured to receive the respiratory effort signal and the respiratory flow signal in real-time, such that the processing unit may process the signals and output determined respiratory timing parameters in real-time.

However, according to an alternative, the processing unit may perform processing of the bio-impedance signal at any time in relation to the acquiring of the respiratory effort signal and the respiratory flow signal. For instance, the respiratory effort signal and the respiratory flow signal may be acquired and gathered during a certain time period, e.g. during night's sleep of the subject. The signals for the entire time period may then be provided to the processing unit, which may synchronize the respiratory effort signal and the respiratory flow signal and then process the signals to output determined respiratory timing parameters. The processing unit may be arranged anywhere, such as making use of processing "in the cloud". The signals may be segmented into sequential sub-segments. Each sub-segment may be separately processed for outputting respiratory timing parameters for each sub-segment processed.

The device may comprise a respiratory effort measurement sensor configured for enabling measurement of a respiratory effort of a subject. Upon measurements, the respiratory effort measurement sensor may output a respiratory effort signal to be received by the processor. For instance, the respiratory effort measurement sensor may include an esophageal manometer, a respiratory inductance plethysmography (RIP) belt, a thoracoabdominal poly-vinylene fluoride (PVDF) belt, an accelerometer, or an electromyograph (EMG) sensor.

The respiratory effort signal may alternatively be acquired using a sensor which is not in direct contact with the subject but may detect movement of the chest of the subject as a measure of respiratory effort. For instance, the respiratory effort measurement sensor may include a sensor for acquiring a radar signal interacting with the subject, a camera imaging the subject, or a pressure sensor may be used. The respiratory effort measurement sensor may be configured to be embedded in a bed/chair in which the subject lies/sits or mounted in a predetermined relation to the bed/chair.

The device may comprise a respiratory flow measurement sensor configured for enabling measurement of a respiratory air flow of a subject. Upon measurements, the respiratory flow measurement sensor may output a respiratory flow signal to be received by the processor. For instance, the respiratory flow measurement sensor may include an oronasal thermal sensor, such as a thermistor, a poly-vinylene fluoride sensor, or a thermocouple, a nasal pressure transducer, a pneumotachograph sensor, or a spirometer.

The device may be provided as a prepared kit of parts, configured to be connected by wired or wireless connection and set up for communicating signals between different parts in the device. Thus, a user may immediately start using the device, without need of connecting parts of the device to external units, which may be provided by other vendors.

However, it should be realized that parts of the device may be provided from different vendors, such that a user may assemble the device and connect different parts to each other for e.g. providing communication of signals between different parts. Further, if the processing unit does not process the signals in real-time, the processing unit may separately receive the respiratory effort signal and the respiratory flow signals. The device may need initial set-up before use.

According to one embodiment, the processing unit is configured to preprocess the respiratory effort signal and the respiratory flow signal before the method according to the first aspect or any embodiments thereof is carried out. The preprocessing of the signals may be for filtering purposes, e.g. for noise removal and/or for removing contribution of cardiac activity in the signals.

The preprocessing of the signals may also or alternatively be for performing one or more of data cleaning, resampling, and shifting of the signals.

It should be further realized that the processing unit may be provided as a single processor, which may execute one or more processing threads for providing processing of received signals. However, the processing unit may also be distributed in a plurality of physical units. For instance, the preprocessing may be performed on a processor arranged in a housing in which the respiratory effort measurement sensor and/or the respiratory flow measurement sensor is placed, which processor may transfer preprocessed signals to a central processor, which may be configured to also receive further signals. Alternatively, in case of bio-impedance measurements, the respiratory effort signal and the respiratory flow signal may be acquired by a central processor configured to divide a bio-impedance signal acquired by bio-impedance measurement sensor, such as electrodes, into the respective effort and flow component.

According to one embodiment, the device may comprise an adhesive patch, a textile/garment being worn by the subject, or a belt, which may be configured to be attached around a torso of the subject. The device may comprise the bio-impedance measurement sensor and arranged so that said sensor is enabled to measure bio-impedance of a subject.

In particular, the device may be a wearable patch device. The processing unit may be arranged in the wearable patch device. The processing unit may alternatively be arranged in a central unit, which may or may not be configured to be worn by the subject. The central unit may be connected by wires or wirelessly to the respiratory effort measurement sensor and the respiratory flow measurement sensor for receiving respiratory effort signal and respiratory flow signal respectively, or to a bio-impedance measurement sensor for receiving a bio-impedance signal from which the respiratory effort signal and the respiratory flow signal is determined.

The wearable patch device may comprise other sensors for measuring respiratory effort and respiratory air flow of a subject.

According to an embodiment, the bio-impedance measurement sensor comprises at least two or at least four electrodes and is configured for bipolar or tetrapolar measurement of the bio-impedance.

In bipolar measurement, the same electrodes may be used both for providing a stimulation signal and for acquiring the bio-impedance signal.

In tetrapolar measurement, two electrodes are used for providing a stimulation signal and two other electrodes are used for acquiring the bio-impedance signal.

The invention is defined by the appended independent claims, with embodiments being set forth in the appended dependent claims, in the following description and in the drawings.

BRIEF DESCRIPTION OF THE DRAWINGS

The invention will in the following be described in more detail with reference to the enclosed drawings, wherein.

DESCRIPTION OF EMBODIMENTS

Figure 1:
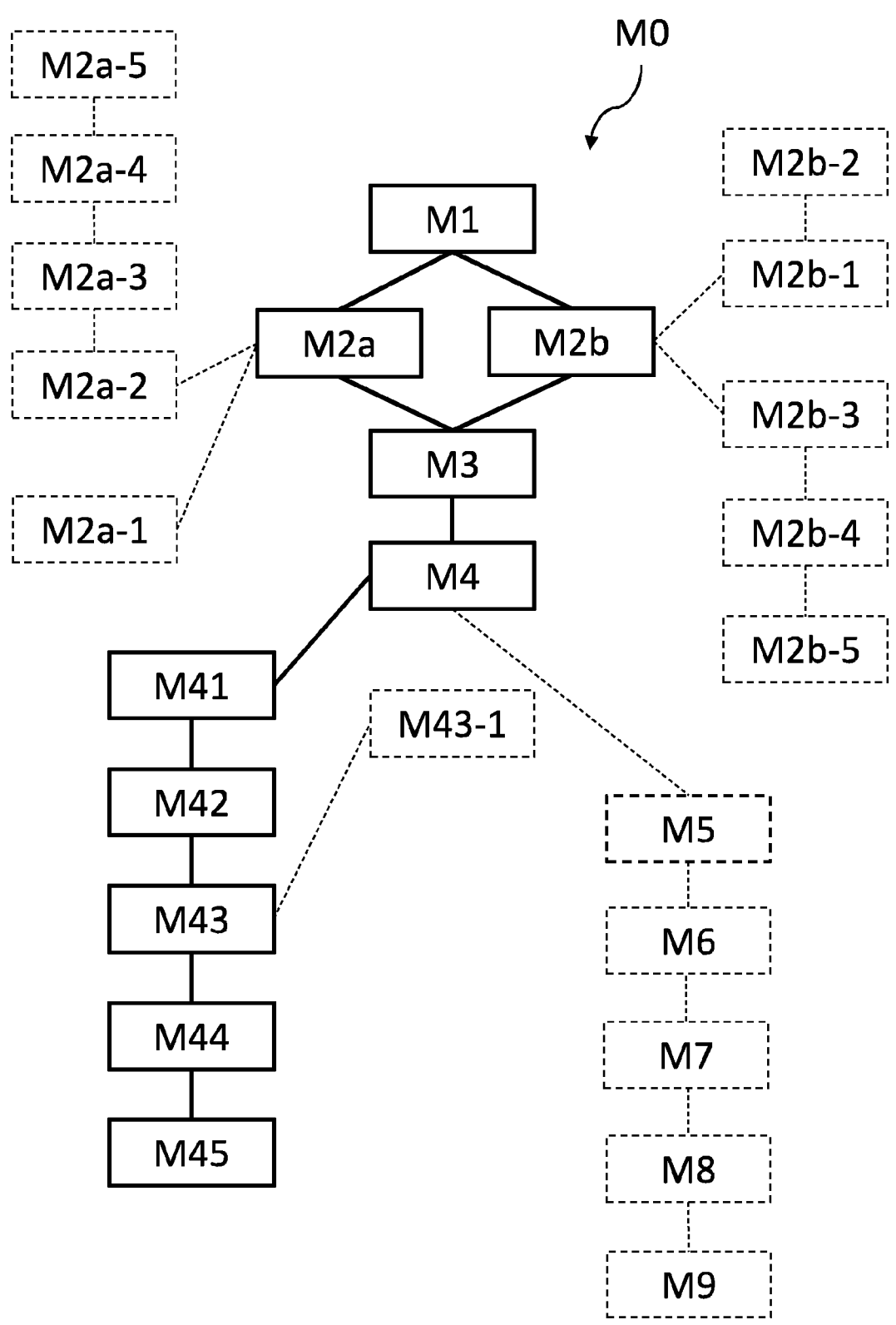
FIG. 1 illustrates a schematic of a method according to one embodiment of the invention; wherein dashed boxes indicates optional embodiments.

The present invention will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. In the drawings, like numbers refer to like elements.

Figure 2:
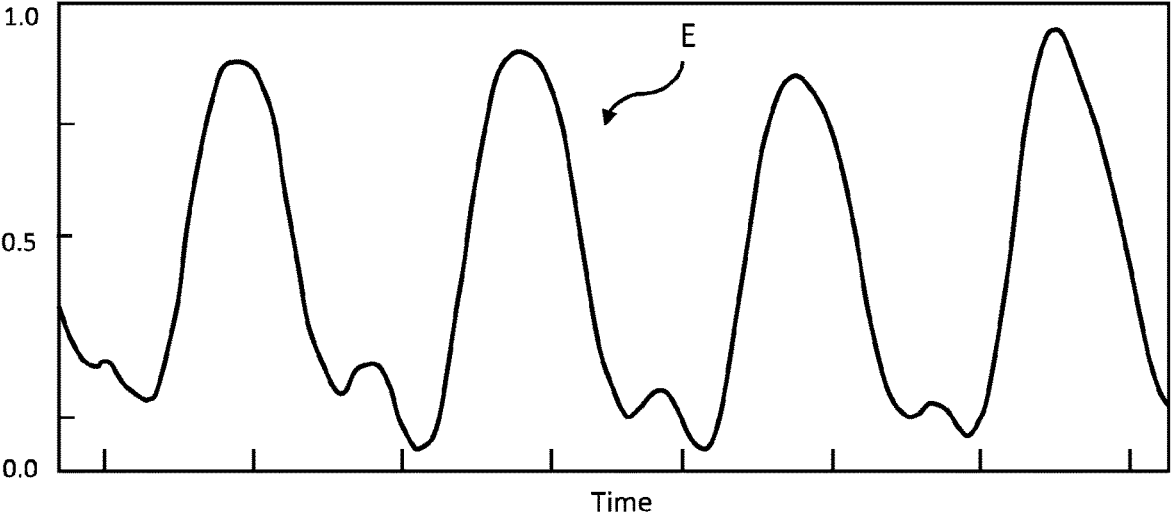
FIG. 2 illustrates a sub-segment of a respiratory effort signal be used as input to the method according to one embodiment of the invention.
Figure 3:
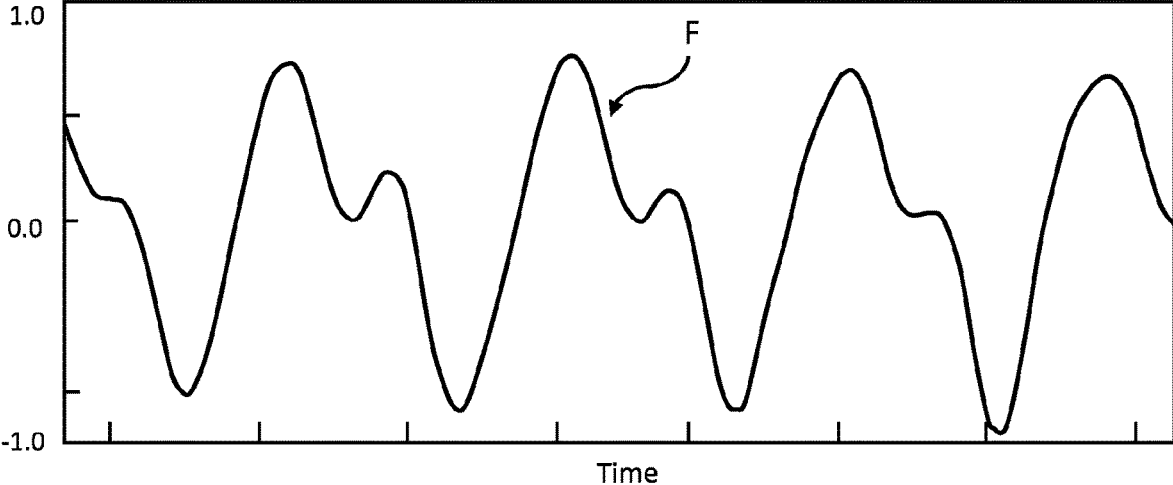
FIG. 3 illustrates a sub-segment of a respiratory flow signal be used as input to the method according to one embodiment of the invention.
Figure 4:
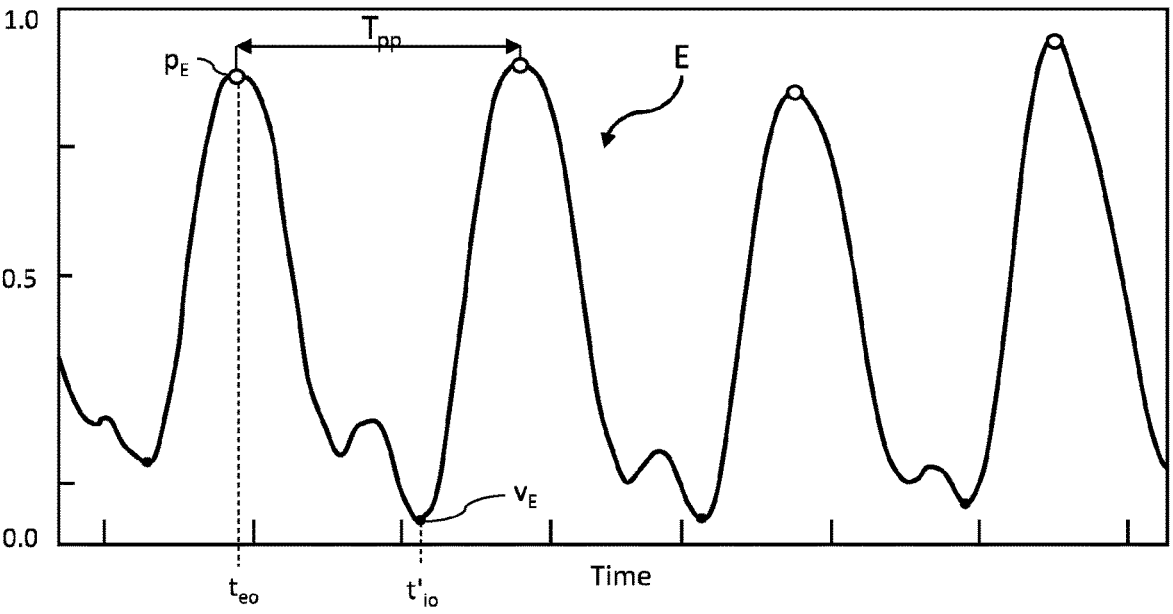
FIG. 4 illustrates a sub-segment of a respiratory effort signal wherein peaks and valleys have been determined according to one embodiment of the invention.

FIG. 1 illustrates a schematic of a method according to one embodiment of the invention; wherein dashed boxes indicates optional embodiments. The method M0 comprises the step of providing M1 a respiratory effort signal E and a respiratory flow signal F of a subject. FIG. 2 and FIG. 3 respectively show examples of such signals. The method M0 further comprises a step of determining M2a an ensemble of peaks IDE in the respiratory effort signal E and a step of determining M2b an ensemble of valleys vE in the respiratory signal E. This can be seen in FIG. 4 which shows a respiratory effort signal E with peaks IDE and valleys $v_E$ indicated. The method also comprises a step of identifying M3 times associated with the valleys $v_E$ as preliminary inspiratory onset times $t'_{io}$. The preliminary inspiratory onset times $t'_{io}$ within respective peak-to-peak intervals $T_{pp}$ of the respiratory effort signal E is then refined in a refinement step M4. This will be explained in the following.

Figure 5:
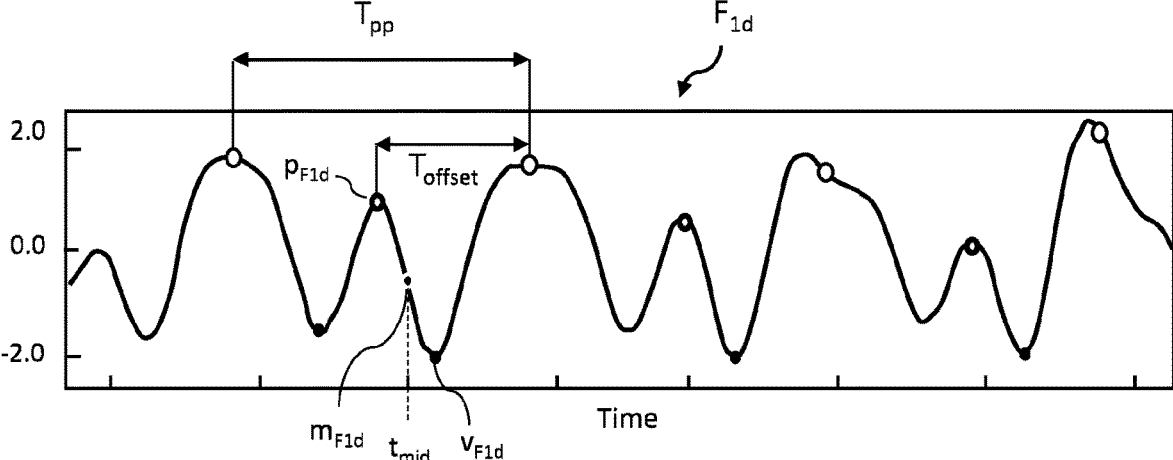
FIG. 5 illustrates a sub-segment of a respiratory flow signal derivative according to one embodiment of the invention.

The refinement step M4 comprises a step M41 of determining $F_{1d}$ of the respiratory flow signal F in a respective peak-to-peak interval $T_{pp}$ and a step of determining M42 local peaks $p_{F1d}$ and valleys $v_{F1d}$ in the respiratory flow signal first derivative $F_{1d}$. The respiratory flow signal derivative $F_{1d}$ is shown in FIG. 5 where peaks $p_{F1d}$ and valleys $v_{F1d}$ of the respiratory flow signal first derivative $F_{1d}$ are indicated. The method further comprises a step of determining M43 a time midpoint $t_{mid}$ between the time of a local valley $v_{F1d}$ in the respiratory flow signal first derivative $F_{1d}$ closest in time to the later endpoint in the respective peak-to-peak time interval $T_{pp}$ and a peak pdf in the respiratory flow signal first derivative $F_{1d}$ in the respective peak-to-peak interval $T_{PP}$. This is shown in FIG. 5 wherein the time midpoint $t_{mid}$ of a midpoint $m_{F1d}$ between a valley $v_{F1d}$ and a peak $p_{F1d}$ is indicated.

Figures 6, 7:
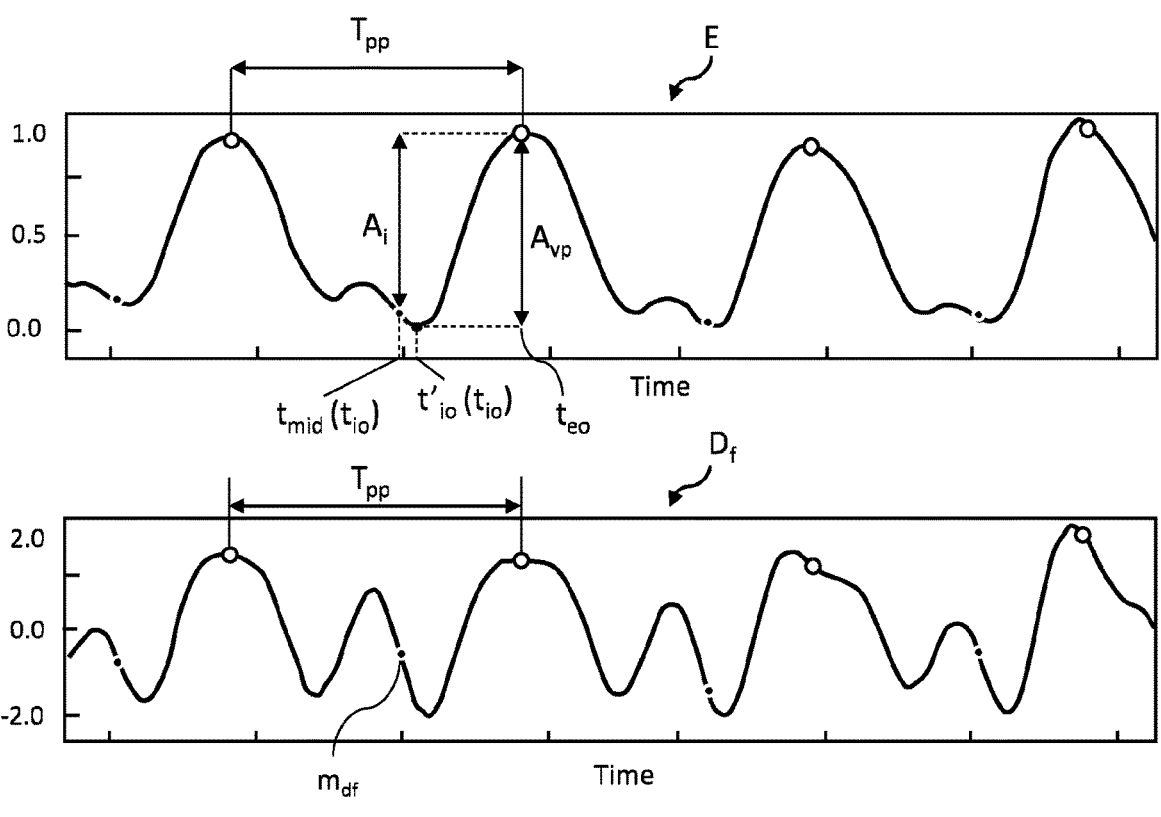
FIG. 6 illustrates a respiratory effort signal and a respiratory flow signal derivative according to one embodiment of the invention.
FIG. 7 illustrates a selection of determined respiratory parameters according to one embodiment of the invention.

The method M0 further comprises a step of evaluating M44 whether the respiratory effort signal E at the determined time midpoint $t_{mid}$ satisfies a predetermined inspiratory onset time condition, and if satisfied, selecting M45 the determined time midpoint $t_{mid}$ as an inspiratory onset time $t_{io}$ instead of the preliminary inspiratory onset time $t'_{io}$ for that peak-to-peak interval $T_{PP}$. This is indicated in FIG. 6 wherein both timepoints $t_{mid}$ and $t'_{io}$ are indicated. Depending on whether the respiratory effort signal E at the determined time midpoint $t_{mid}$ satisfies the predetermined inspiratory onset, either the time midpoint or the preliminary inspiratory onset time will be selected as the inspiratory onset time $t_{io}$.

This is done for a plurality of such peak-to-peak time intervals, thereby resulting in an ensemble of inspiratory onset times $t_{io}$ some of which may have been refined. Such ensemble of inspiratory onset times $t_{io}$ may then by used in further respiration analysis.

As is explained in the summary of this disclosure, the respiratory effort signal E and the respiratory flow signal F may be provided via a number of devices, each of which are characterized by advantages which may be beneficial to the disclosed method. In a preferred embodiment, the respiratory effort signal E and the respiratory flow signal F are obtained via non-invasive respiratory monitoring measurements. In particular, the respiratory effort signal E and the respiratory flow signal F are obtained via bio-impedance signal measurements.

The predetermined inspiratory onset time condition may be selected differently depending on the situation but according to a preferred embodiment, the predetermined inspiratory onset time condition is whether the amplitude range $A_i$ of the inspiratory effort signal E at the inspiratory onset time $t_{io}$ to the subsequent expiratory onset time $t_{eo}$ is at least 75% of the amplitude range $A_{vp}$ of the respiratory effort signal E as measured from the preliminary inspiratory onset time $t'_{io}$, i.e. from a valley, to the following expiratory onset time $t_{eo}$, i.e. a peak. This is shown in the upper graph of FIG. 6.

Further, the step of determining M41 first derivative of the respiratory flow signal F preferably includes using a Savitsky-Golay derivative kernel incorporating a $2^{nd}$ degree polynomial fit. The Savtizky-Golay derivative kernel may for example be characterized by a frame length equal to or less than 150 ms, preferably less than 120 ms. The figures represent data wherein a Savitsky-Golay derivative kernel incorporating a $2^{nd}$ degree polynomial fit was used, and also wherein the frame length was set to 110 ms.

Figure 8:
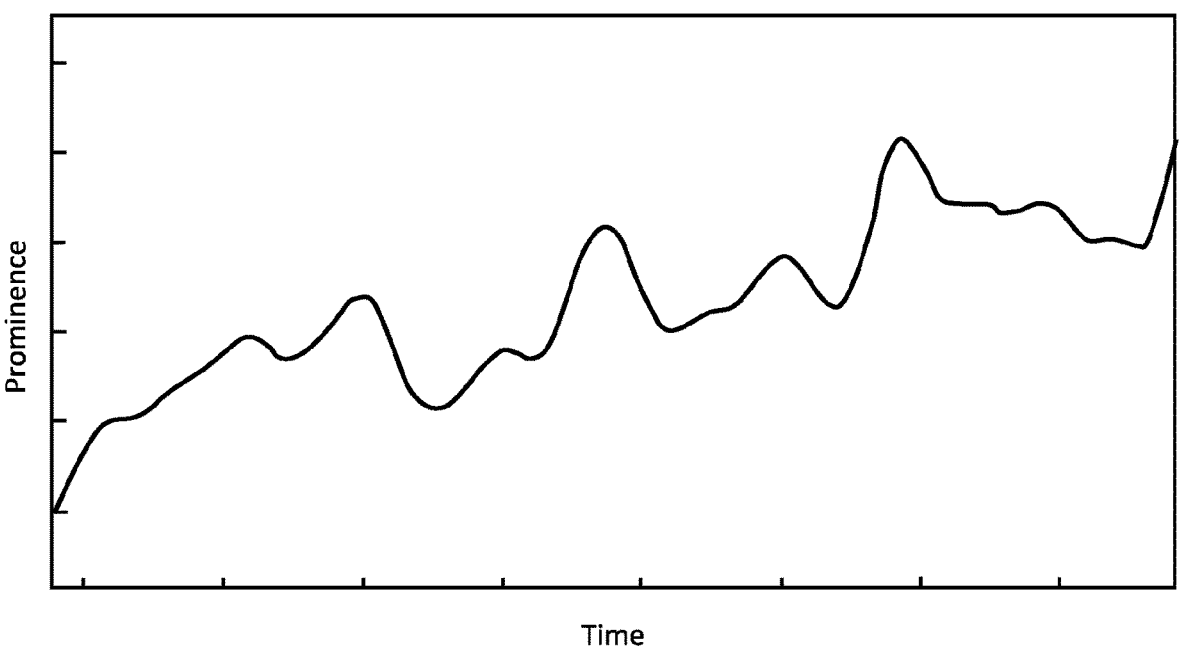
FIG. 8 illustrates prominence determined over the same sub-segment of the respiratory effort signal shown in previous figures, the prominence as determined according to one embodiment of the invention.

According to one embodiment, the step of determining M2a an ensemble of peaks in the respiratory effort signal E includes selecting M2a-1 peaks determined to have a prominence greater than an average prominence determined over a sub-segment of the respiratory effort signal E. The prominence for a sub-segment is shown in FIG. 8 and the average prominence is then determined over this subsegment and only peaks who has a prominence greater than the average prominence is considered. The average prominence may be determined as mentioned in the summary. The valleys $v_E$ of the respiratory effort signal E may be determined in a similar manner; wherein the step of determining M2b an ensemble of valleys in the respiratory effort signal E includes inverting M2b-1 a sub-segment of the respiratory effort signal E and selecting M2b-2 peaks determined to have a prominence greater than an average prominence determined over said inverted sub-segment.

In a preferred embodiment, the method comprises the step of determining M2a-2 if there is missing any determined valleys between any two consecutive peaks in the ensemble of peaks, and if so, inverting M2a-3 the two-consecutive-peak segment missing a determined valley and determining M2a-4 the location of the undetermined valley by peak detection using half of the two-consecutive-peak segment's dynamic range as a minimum prominence threshold, and if unable to determine a valley still, determining M2a-5 the location of the undetermined valley as the midpoint between the two consecutive peaks. This increases the likelihood that there is an equal set of inspiratory onset times and expiratory onset times obtained, and that each onset times are determined in a correct manner.

Likewise, the method may comprise the step of determining M2b-3 if there is missing any determined peaks between any two consecutive valleys in the ensemble of valleys, and if so, determining M2b-4 the location of the undetermined peak in the two-consecutive-valley segment's dynamic range as a minimum prominence threshold, and if unable to determine a peak still, determining M2b-5 the location of the undetermined peak as the midpoint between the two consecutive valleys.

According to one embodiment, the step of determining M42 local peaks $p_{F1d}$ and valleys $v_{F1d}$ in the respiratory flow signal first derivative $F_{1d}$ includes using more than a predetermined ratio of a local dynamic range as minimum peak prominence. The predetermined ratio may be equal to or more than 5-10%. To obtain the data for represented in some figures, a predetermined ratio of 5% or 1/20 was used.

In a preferred embodiment, as indicated in FIG. 1, the step of determining M43 a time midpoint $t_{mid}$ includes using M43-1 peaks in the respiratory flow signal first derivative $F_{1d}$ which are closest, but no closer than a predetermined time offset $T_{offset}$, to the latest endpoint of the respective peak-to-peak time interval $T_{PP}$. The predetermined time offset $T_{offset}$ may be less than 200 milliseconds, preferably less than 160 milliseconds. This is shown in FIG. 5 wherein the $T_{offset}$ is indicated. To obtain the data for represented in some figures, a time offset $T_{offset}$=156 milliseconds was used.

The method M0 may also comprise the step of identifying M5 times associated with the peaks of the ensemble of peaks $p_E$ of the respiratory effort signal E as expiratory onset times $t_{eo}$ and determining M6 whether the inspiratory onset times $t_{io}$ and the expiratory onset times $t_{eo}$ are qual in number. Expiratory onset times $t_{eo}$ are indicated in FIG. 2. Both expiratory onset times $t_{eo}$ and inspiratory onset times $t_{io}$ are indicated in upper graph of FIG. 6.

The expiratory onset times $t_{eo}$ and the inspiratory onset times $t_{io}$ may be used to determine a number of respiratory timing parameters. For example, the method M0 may comprise the step of determining M6 a first respiration parameter being an inspiratory time interval by taking expiratory onset time and subtracting from it the inspiratory onset time. Also, the method may comprise the step of determining M7 a second respiration parameter being an expiratory time interval by taking inspiratory onset time and subtracting from it the expiratory onset time. Using these, further respiratory timing parameters may be determined, thus, the method according to one further embodiment may comprise the step of determining M8 a respiratory rate by taking the reciprocal of the sum of the inspiratory onset time interval and the expiratory time interval, or alternatively, a respiratory rate by taking the reciprocal of the time interval between two adjacent peaks (expiratory onset times) of the respiratory effort signal, or alternatively, a respiratory rate by taking the reciprocal of the time interval between two adjacent valleys (inspiratory onset times) of the respiratory effort signal, or alternatively, a respiratory rate obtained by combining the time-course of reciprocal of the time-interval between two adjacent peaks and the time-course of the reciprocal of the time-interval of two adjacent valleys. Also, the method M0 may comprises the step of determining M9 an inspiratory duty cycle by multiplying the inspiratory time interval with the respiratory rate. The respiratory rate, the inspiratory time interval Ti and the expiratory time interval Te, and the duty cycle are each shown in FIG. 7.

Figure 9:
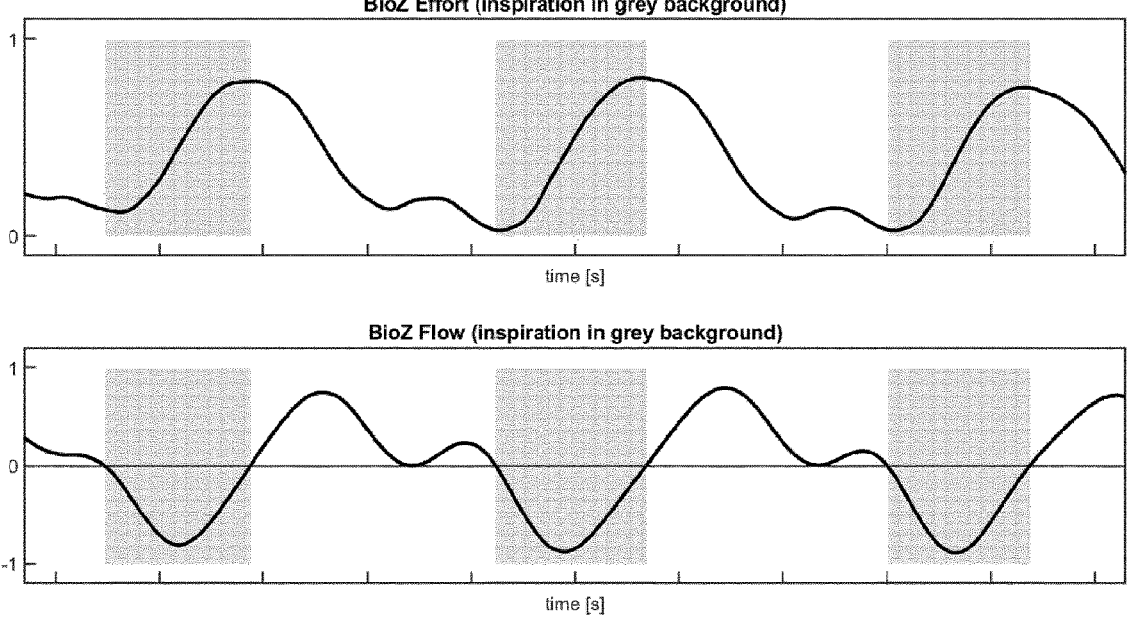
FIG. 9 illustrates expiration and inspiration periods determined according to one embodiment of the invention.

With such respiratory timing parameters, it may thus be possible to indicate expiration and inspiration phases in the respiratory effort signal E and the respiratory flow signal F as done in FIG. 9. Here, inspiration is indicated by grey backgrounds.

The method M0 may be provided as instructions in a computer program which, when executed by a computing device, cause the computing device to carry out the method according to first aspect or any embodiments thereof. The computing device may be a portable computing device such as a smartphone, a smartwatch, a tablet, or a laptop. The computing device may alternatively be a workstation or a server. In case of a server, the program code may be controlled from an interface running on a remote computing device. The program code may be executed by means of cloud computing.

Figure 10:
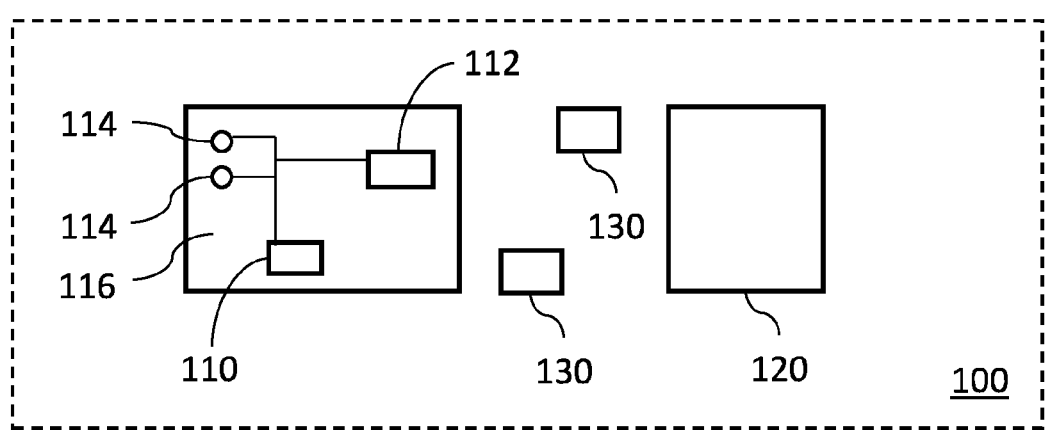
FIG. 10 illustrates a schematic of a device according to one embodiment of the invention.
Figure 11:
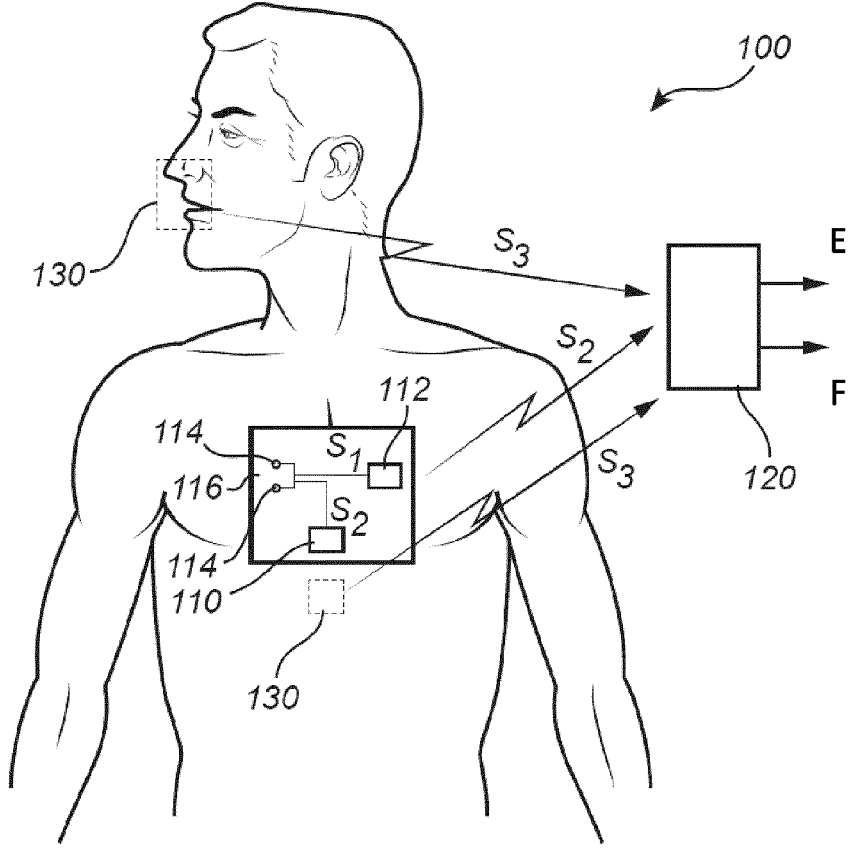
FIG. 11 illustrates a device according to one embodiment of the invention while arranged on a subject.

FIG. 10 shows a device for providing respiratory parameters from respiration monitoring measurements. As shown in FIG. 1, the device 100 comprises a current signal injection module 112. The current signal injection module 112 may be configured to generate and output the current signal S1, which is to be applied to the subject. The current signal injection module 112 may comprise a current source for generating a current signal S1. The current signal injection module 112 may be configured to output an AC current signal. The device 100 further comprises a bioimpedance measurement sensor 110. The bioimpedance measurement sensor 110 may be configured to receive voltage input signals representing a voltage generated by the current signal S1 applied to the subject. The bioimpedance measurement sensor 110 may be configured to extract a measured bioimpedance signal S2 from the received voltage input signals. The bioimpedance measurement sensor 110 may be configured to process the received voltage input signals, e.g. by filtering the input signals, in order to extract relevant information.

The bioimpedance measurement sensor 110 may comprise two or more electrodes 114, which may be arranged to be in contact with skin of the subject. The electrodes 114 may be connected to the current signal injection module 112 to receive the current signal S1 and provide the current signal through tissue of the subject. The electrodes 114 may also be connected to the bioimpedance measurement sensor 110 for providing voltage input signals that may be used for measuring the bioimpedance signal S2. The electrodes 114 may be arranged in a bipolar arrangement, wherein the same electrodes 114 are used for providing the current signal S1 to the subject and for acquiring the voltage input signals. However, the electrodes 114 may alternatively be arranged in a tetrapolar arrangement, wherein two electrodes are used for providing the current signal S1 to the subject and two other electrodes are used for acquiring the voltage input signals.

More than two (or four) electrodes 114 may be provided, which may allow selection of which electrodes 114 to be used in a measurement, so that electrodes 114 providing highest quality bioimpedance signal S2 may be selected. The selection of which electrodes 114 to be used may be performed in set-up of the device 100 or may be dynamically changed during signal acquisition e.g. when conditions for acquiring the bioimpedance signal change. The bioimpedance measurement sensor 110 with electrodes 114 may be configured to be attached on a thorax region of the subject. The bioimpedance measurement sensor 110 may be arranged on a patch device 116 configured for being arranged on a thorax region of the subject, wherein the electrodes 114 may be mounted to be exposed on the patch device 116, such that the electrodes 114 may be arranged in contact with the skin of the subject. The patch device 116 may for instance comprise an adhesive patch, a textile/garment being worn by the subject, or a belt, which may be configured to be attached around the torso of the subject.

When a bioimpedance measurement is performed based on electrodes 114 arranged on the thorax of a subject, chest expansion may cause a change in a current path between the electrodes 114, such that the bioimpedance is changed in relation to a respiratory effort. Also, air has a different impedance than tissue. As an amount of air present in the lungs varies during a respiratory cycle, the bioimpedance is also changed in relation to respiratory airflow. Thus, the bioimpedance measurement sensor 110 may be configured for acquisition of a bioimpedance signal S2 which holds information of both respiratory effort and respiratory airflow. The processing unit 120 may be configured to receive the bioimpedance signal S2 from the bioimpedance measurement sensor 110. The processing unit may be further configured to process the bio-impedance signal S2 to extract therefrom a respiratory effort signal E and a respiratory flow signal F. These may then be used by a processing unit configured to execute the method herein disclosed. The processing unit may be the same processing unit extracting the respiratory effort signal E and the respiratory flow signal F.

In an optional embodiment, the processing unit 120 may further be configured to receive a reference signal S3 from a reference measurement sensor 130. The reference signal S3 may be acquired so as to isolate respiratory effort from respiratory airflow, e.g. by using a sensor which is placed or configured for acquiring a signal which is only affected by either respiratory effort or respiratory airflow. Hence, the reference signal S3 may represent respiratory effort or respiratory airflow.

The processing unit 120 may be implemented in hardware, or as any combination of software and hardware. The processing unit 120 may, for instance, be implemented as software being executed on a general-purpose computer. The device 100 may thus comprise one or more physical processors, such as a central processing unit (CPU), which may execute the instructions of one or more computer programs in order to implement functionality of the processing unit 120. Thus, the device 120 may comprise a single processing unit, which may provide a plurality of functionalities e.g. as separate threads within the processing unit 120. The processing unit 120 may alternatively be implemented as firmware arranged e.g. in an embedded device, or as a specifically designed processing unit, such as an Application-Specific Integrated Circuit (ASIC) or a Field-Programmable Gate Array (FPGA). The reference measurement sensor 130 may be part of and may be delivered with the device 100. The device 100 may thus be set-up for communication between the reference measurement sensor 130 and the processing unit 120. However, the reference measurement sensor 130 may alternatively be separately delivered, e.g. by a different vendor than the vendor providing the device 100. A user may thus connect the reference measurement sensor 130 to the processing unit 120, e.g. by attaching a wire between the reference measurement sensor 130 and a port in a housing in which the processing unit 120 is arranged, whereby the processing unit 120 and the reference measurement sensor 130 may then exchange set-up messages for automatically setting up communication between each other. Alternatively, a user may initiate a discovery procedure for allowing a wireless communication between the reference measurement sensor 130 and the processing unit 120 to be established and again for automatically setting up communication between the reference measurement sensor 130 and the processing unit 120. In a further alternative, the reference measurement sensor 130 and the bioimpedance measurement sensor 110 may be configured to separately communicate the reference signal S3 and the bioimpedance signal S2 to a remotely arranged processing unit 120, e.g. a processing unit 120 arranged "in the cloud". The signals may be communicated after an entire period of gathering the signals, such as signals acquired during a night's sleep of the subject. The processing unit 120 may then synchronize the signals before processing.

A reference measurement sensor 130 configured to acquire a reference signal representing a respiratory effort may be any sensor which may be configured to acquire a representation of the respiratory effort. For instance, the reference measurement sensor 130 may include an esophageal manometer, a respiratory inductance plethysmography (RIP) belt, a thoracoabdominal polyvinylene fluoride (PVDF) belt, an accelerometer, or an electromyograph (EMG) sensor.

A reference measurement sensor 130 configured to acquire a reference signal representing a respiratory airflow may be any sensor which may be configured to acquire a representation of the respiratory airflow. For instance, reference measurement sensor may include an oro-nasal thermal sensor, such as a thermistor, a polyvinylene fluoride sensor, or a thermocouple, a nasal pressure transducer, a pneumotachograph sensor, or a spirometer. The processing unit 120 may be configured to receive reference signals S3 from a plurality of reference measurement sensors 130. The plurality of reference measurement sensors 130 may comprise only sensors configured to acquire a reference signal S3 representing respiratory effort, only sensors configured to acquire a reference signal S3 representing respiratory airflow, or one or more sensors configured to acquire a reference signal S3 representing respiratory effort combined with one or more sensors configured to acquire a reference signal S3 representing respiratory airflow. To illustrate these options, reference measurement sensors 130 are indicated by dashed lines in FIG. 1.

The device 100 may comprise one or more housings, in which the bioimpedance measurement sensor 110, the processing unit 120 and the reference measurement sensor 130 may be arranged. The housings may be connected by wires for allowing communication between the sensors and the processing unit 120. Alternatively, one or more of the sensors 110, 130 and the processing unit 120 may be set up for wireless communication. The device 100 may thus be delivered to be ready to use, e.g. in a single package with all parts of the device 100 already set up to communicate with each other.

The processing unit 120 may be arranged in a housing on the patch device 116. The reference measurement sensor 130 may also be arranged on the same patch device 116. However, in an alternative embodiment, the processing unit 120 may be arranged in a central housing, which may be separate from the patch device 116. The central housing may further comprise an output port for connection to an external unit, which may receive the respiratory effort signal E and the respiratory flow signal F for further processing of the components. Alternatively, or additionally, the central housing may comprise a communication unit for wireless communication of the respiratory effort signal E and the respiratory flow signal F to the external unit. The central housing may also be connected to a display for enabling the respiratory effort signal E and the respiratory flow signal F to be output on the display. Also, the reference signal may be output on the display S3. This may allow a physician, nurse or any other person, to manually inspect signals representing respiration of the subject, e.g. for manual analysis of the respiration.

In the drawings and specification, there have been disclosed preferred embodiments and examples of the invention and, although specific terms are employed, they are used in a generic and descriptive sense only and not for the purpose of limitation, the scope of the invention being set forth in the following claims.

The invention claimed is:

1. A computer-implemented method for generating respiratory timing parameters from respiratory monitoring measurements of a subject, the method performed by one or more processors and comprising the steps of:

receiving a respiratory effort signal of a subject from at least one respiratory effort measurement sensor and a respiratory flow signal of the subject from at least one respiratory flow measurement sensor, processing the respiratory effort signal to identify an ensemble of peaks and an ensemble of valleys in the respiratory effort signal;

identifying times associated with the valleys in the respiratory effort signal as preliminary inspiratory onset times;

segmenting the respiratory effort signal into peak-to-peak time intervals based on the identified peaks and valleys; and refining the preliminary inspiratory onset times within respective peak-to-peak time intervals of the respiratory effort signal by:

calculating a first derivative of the respiratory flow signal in a respective peak-to-peak interval, identifying local peaks and valleys in the respiratory flow signal first derivative, calculating a time midpoint between the time of a local valley in the respiratory flow signal first derivative closest in time to the later endpoint in the respective peak-to-peak time interval and the time of a local peak in the respiratory flow signal first derivative in the respective peak-to-peak time interval, and determining whether the respiratory effort signal at the calculated time midpoint satisfies a predetermined inspiratory onset time condition, and if satisfied, selecting the calculated time midpoint as an inspiratory onset time instead of the preliminary inspiratory onset time for that peak-to-peak interval, whereas if the condition is not satisfied, keeping the preliminary inspiratory onset time as the inspiratory onset time for that peak-to-peak interval.

2. The method according to claim 1, wherein the respiratory effort signal and the respiratory flow signal are obtained via non-invasive respiratory monitoring measurements.

3. The method according to claim 1, wherein the respiratory effort signal and the respiratory flow signal are obtained via bio-impedance signal measurements.

4. The method according to claim 1, wherein the predetermined inspiratory onset time condition is whether an amplitude range of the respiratory effort signal from the calculated time midpoint to the later endpoint in the respective peak-to-peak time interval is at least 75% of a valley-to-peak amplitude range of the respiratory effort signal in the respective peak-to-peak time interval.

5. The method according to claim 1, wherein the step of calculating the first derivative of the respiratory flow signal includes using a Savitsky-Golay derivative kernel incorporating a $2^{nd}$ degree polynomial fit.

6. The method according to claim 5, wherein the Savitsky-Golay derivative kernel is characterized by a frame length equal to or less than 150 ms.

7. The method according to claim 1, wherein the step of identifying the ensemble of peaks in the respiratory effort signal includes selecting peaks determined to have a prominence greater than an average prominence determined over a sub segment of the respiratory effort signal.

8. The method according to claim 1, wherein the step of identifying the ensemble of valleys in the respiratory effort signal includes inverting a sub segment of the respiratory effort signal and selecting peaks determined to have a prominence greater than an average prominence determined over said inverted sub segment.

9. The method according to claim 7, wherein a length of the sub segment is between 10 and 15 seconds.

10. The method according to claim 1, further comprising the step of:

determining if any identified valleys are missing between any two consecutive peaks in the ensemble of peaks, and if so, inverting the two-consecutive-peak segment missing a determined valley, and determining a location of an undetermined valley by peak detection using half of the two-consecutive-peak segment's dynamic range as a minimum prominence threshold, and if unable to determine a valley still, determining the location of the undetermined valley as the midpoint between the two consecutive peaks.

11. The method according to claim 1, further comprising the step of:

determining if any determined peaks are missing between any two consecutive valleys in the ensemble of valleys, and if so, determining a location of an undetermined peak in the two-consecutive-valley segment missing a determined peak by peak detection using half of the two-consecutive-valley segment's dynamic range as a minimum prominence threshold, and if unable to determine a peak still, determining the location of the undetermined peak as the midpoint between the two consecutive valleys.

12. The method according to claim 1, wherein the step of identifying peaks and valleys in the respiratory flow signal first derivative includes using more than a predetermined ratio of a local dynamic range as minimum peak prominence.

13. The method according to claim 1, wherein the step of calculating the time midpoint includes using peaks in the respiratory flow signal first derivative which are the closest, but which are no closer than a predetermined time offset, to the latest later endpoint of the respective peak-to-peak time interval.

14. The method according to claim 1, further comprising the step of:

identifying times associated with the peaks of the ensemble of peaks of the respiratory effort signal as expiratory onset times.

15. The method according to claim 6, wherein the Savitsky-Golay derivative kernel is characterized by a frame length less than 120 ms.

16. The method according to claim 12, wherein the predetermined ratio is equal to or more than 5-10%.

17. The method according to claim 1, wherein the step of calculating the time midpoint includes using peaks in the respiratory flow signal first derivative which are the closest, but no closer than a predetermined time offset, to the later endpoint of the respective peak-to-peak time interval, and wherein the predetermined time offset is less than 200 milliseconds.

18. The method according to claim 1, wherein the step of calculating the time midpoint includes using peaks in the respiratory flow signal first derivative which are the closest, but no closer than a predetermined time offset, to the later endpoint of the respective peak-to-peak time interval, and wherein the predetermined time offset is less than 160 milliseconds.

19. The method according to claim 1, further comprising the steps of:

identifying times associated with the peaks of the ensemble of peaks of the respiratory effort signal as expiratory onset times, and determining whether the inspiratory onset times and the expiratory onset times are equal in number.

20. A computer program comprising instructions which, when executed by a computing device, cause the computing device to carry out a method for generating respiratory timing parameters from respiratory monitoring measurements of a subject, the method comprising the steps of:

receiving a respiratory effort signal of a subject from at least one respiratory effort measurement sensor and a respiratory flow signal of the subject from at least one respiratory flow measurement sensor;

processing the respiratory effort signal to identify an ensemble of peaks and an ensemble of valleys in the respiratory effort signal;

identifying times associated with the valleys in the respiratory effort signal as preliminary inspiratory onset times;

segmenting the respiratory effort signal into peak-to-peak time intervals based on the identified peaks and valleys; and refining the preliminary inspiratory onset times within respective peak-to-peak time intervals of the respiratory effort signal by:

calculating a first derivative of the respiratory flow signal in a respective peak-to-peak interval, identifying local peaks and valleys in the respiratory flow signal first derivative, calculating a time midpoint between the time of a local valley in the respiratory flow signal first derivative closest in time to the later endpoint in the respective peak-to-peak time interval and the time of a local peak in the respiratory flow signal first derivative in the respective peak-to-peak time interval, and determining whether the respiratory effort signal at the calculated time midpoint satisfies a predetermined inspiratory onset time condition, and if satisfied, selecting the calculated time midpoint as an inspiratory onset time instead of the preliminary inspiratory onset time for that peak-to-peak interval, whereas if the condition is not satisfied, keeping the preliminary inspiratory onset time as the inspiratory onset time for that peak-to-peak interval.

\* \* \* \* \*